(12) United States Patent
Degroot et al.

(10) Patent No.: US 7,110,813 B2
(45) Date of Patent: Sep. 19, 2006

(54) ACTIVATION OF FIBRILLATION AND TACHYCARDIA FUNCTIONS

(75) Inventors: Paul J. Degroot, Brooklyn Park, MN (US); Kevin T. Ousdigian, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 483 days.

(21) Appl. No.: 10/413,001

(22) Filed: Apr. 15, 2003

(65) Prior Publication Data

US 2004/0210255 A1 Oct. 21, 2004

(51) Int. Cl.
*A61N 1/38* (2006.01)
(52) U.S. Cl. .................. 607/5; 607/9; 607/59
(58) Field of Classification Search .............. 607/5, 607/30, 32, 59, 60
See application file for complete search history.

(56) References Cited

U.S. PATENT DOCUMENTS 5,144,947 A 9/1992 Wilson
5,159,926 A 11/1992 Ljungstroem
5,884,743 A 3/1999 Kleifges et al.
5,891,178 A 4/1999 Mann et al.
6,058,326 A * 5/2000 Hess et al. ............. 607/9
6,952,612 B1 * 10/2005 Lu ........................ 607/30

* cited by examiner

*Primary Examiner*—Robert E. Pezzuto
*Assistant Examiner*—Eric D. Bertram
(74) *Attorney, Agent, or Firm*—Michael C. Soldner; Girma Wolde-Michael

(57) ABSTRACT

An implantable medical device may be programmed by a programmer to apply a variety of ventricular fibrillation (VF) and ventricular tachycardia (VT) therapies, such as antitachycardia pacing (ATP) and cardioversion shocks. In general, the invention is directed to automatic activation of VF- and VT-related functions upon a single command. When a clinician interacts with the programmer to set VF therapies to active status, for example, VT therapies are automatically set to active status as well. Activation of several VF- and VT-related functions with a single command may save considerable time and may be beneficial to the patient. The invention further provides the freedom to customize the functions to the particular needs of a single patient or a group of patients.

11 Claims, 7 Drawing Sheets

ACTIVATION OF FIBRILLATION AND TACHYCARDIA FUNCTIONS

TECHNICAL FIELD

The invention relates to implantable medical devices, and more particularly, to implantable medical devices that treat ventricular fibrillation.

BACKGROUND

Ventricular fibrillation (VF) is a life-threatening condition in which the cardiac cells in one or both ventricles of the heart of a patient contract in a random and uncoordinated fashion. During an episode of VF, the heart is unable to pump blood. VF rarely terminates spontaneously. Patients at risk of VF may receive an implantable medical device (IMD), such as a pacemaker-defibrillator, that can detect VF and apply defibrillation therapy to terminate the episode. VF will cause death in a short period of time unless terminated.

Many patients that are at risk of developing VF are also at risk of experiencing tachycardia. Tachycardia is an abnormal heart rhythm characterized by rapid activation of one or more chambers of the heart. Tachycardia is often qualified by the locus of origin: a tachycardia that originates in the ventricles of the heart is called a ventricular tachycardia (VT) and a tachycardia that originates in the atria of the heart is called an atrial tachycardia (AT) or a supraventricular tachycardia (SVT). Some VTs, if untreated, may accelerate into VF, in which the pumping ability of the heart is seriously impaired.

In some patients, VT or AT may respond well to anti-tachycardia pacing (ATP), in which small electric stimulations from an implantable pulse generator (IPG) in an IMD disrupt the propagation of electrical signals that cause the tachycardia. The IMD may be programmed to administer several forms of ATP therapies, and may apply one ATP therapy after another until the tachycardia terminates. Tachycardia therapies may also include the application of a higher voltage cardioversion shock to terminate the tachycardia.

A conventional IMD that includes the capability to treat VF also includes the capability to treat VT with ATP and/or with a shock. When the IMD is implanted, however, all VF- and VT-related functions are "off" to avoid inadvertent therapy delivery during device manipulation that may accompany implantation. At the end of the IMD implant procedure, a clinician such as an electrophysiologist, activates the detection functionality and the therapies that are believed will be beneficial or appropriate to the patient. The clinician may use a programmer that communicates wirelessly with the IMD to program the IMD and activate the therapies. With a conventional IMD and a conventional programmer, each therapy is turned "on" individually, i.e., a clinician sets each therapy to active status on a therapy-by-therapy basis.

SUMMARY

In general, the invention is directed to automatic activation of VF- and VT-related functions upon a single command. In an exemplary embodiment, the invention is directed to automatic activation of VT and VF therapies when VF detection is activated. In addition to activation of the therapies, the command may also activate additional functionality, such as detection routines that detect and discriminate VF and VT.

When a conventional IMD is activated with a programmer, each therapy may be individually activated. Activation of several therapies may require considerable time from the clinician. The invention provides techniques by which a clinician may activate several therapies at a time. The clinician may still activate those therapies that are believed will be beneficial to the patient, but may do so more quickly and efficiently.

With the invention, the clinician may activate a group of default functions by making a single command. The clinician may, for example, set VF detection to active status, and this single command sets default VF therapies to active status and default VT detection and VT therapies to active status as well. Alternatively, the clinician may select a "master 'on'" option that sets the group of functions to active status.

The clinician may further customize the functions to the particular needs of the patient. Should the clinician wish to deactivate certain therapies, for example, or change the hierarchy of ATP therapies, the invention provides the programmer with the option to allow the clinician to make those changes. The invention further provides the programmer with a feature to allow the clinician to make changes to the default set of functions.

In one embodiment, the invention is directed to a method comprising receiving a single command to set a group of functions to active status and setting the group of functions to active status in response to the command. The group of functions comprises at least one of a VF therapy and a VT therapy, but may include other VF- and VT-related functions as well. The method may further include establishing a communication link with an implantable medical device and activating the group of functions in the implantable medical device.

In another embodiment, the invention presents a method comprising retrieving a default function, receiving a command to modify the default function, and modifying the function according to the command. The default function includes at least one of a VF therapy and a VT therapy, and the default function is included in a group of functions that is set to active status by a single command.

In other embodiments, the invention is directed to a computer-readable medium containing instructions for carrying out the techniques described above.

In an additional embodiment, the invention is directed to a device comprising an input device to receive a single command to set a group of functions to active status and a processor to set the group of functions to active status in response to the command. The device may be a programmer that programs an IMD, and may include a communication module to establish a communication link with the IMD.

The invention may result in a substantial saving of time for the clinician, who need not set each therapy to active status on a therapy-by-therapy basis. Instead, the clinician may set several functions to active status with a reduced number of commands. The invention further provides freedom to the clinician to tailor the functions to the particular needs of the patient, as well as to the particular preferences of the clinician.

The invention may also result in improved patient safety, because the invention may reduce the likelihood that therapies may be inadvertently left deactivated. Patients at risk of VF may also benefit from having VT-related functions activated automatically. Activation of ATP therapies may cause the patient to experience fewer episodes of VF, and consequently fewer shocks to treat VF, because some ventricular ATP therapies are known to terminate episodes of VT that may accelerate into VF.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
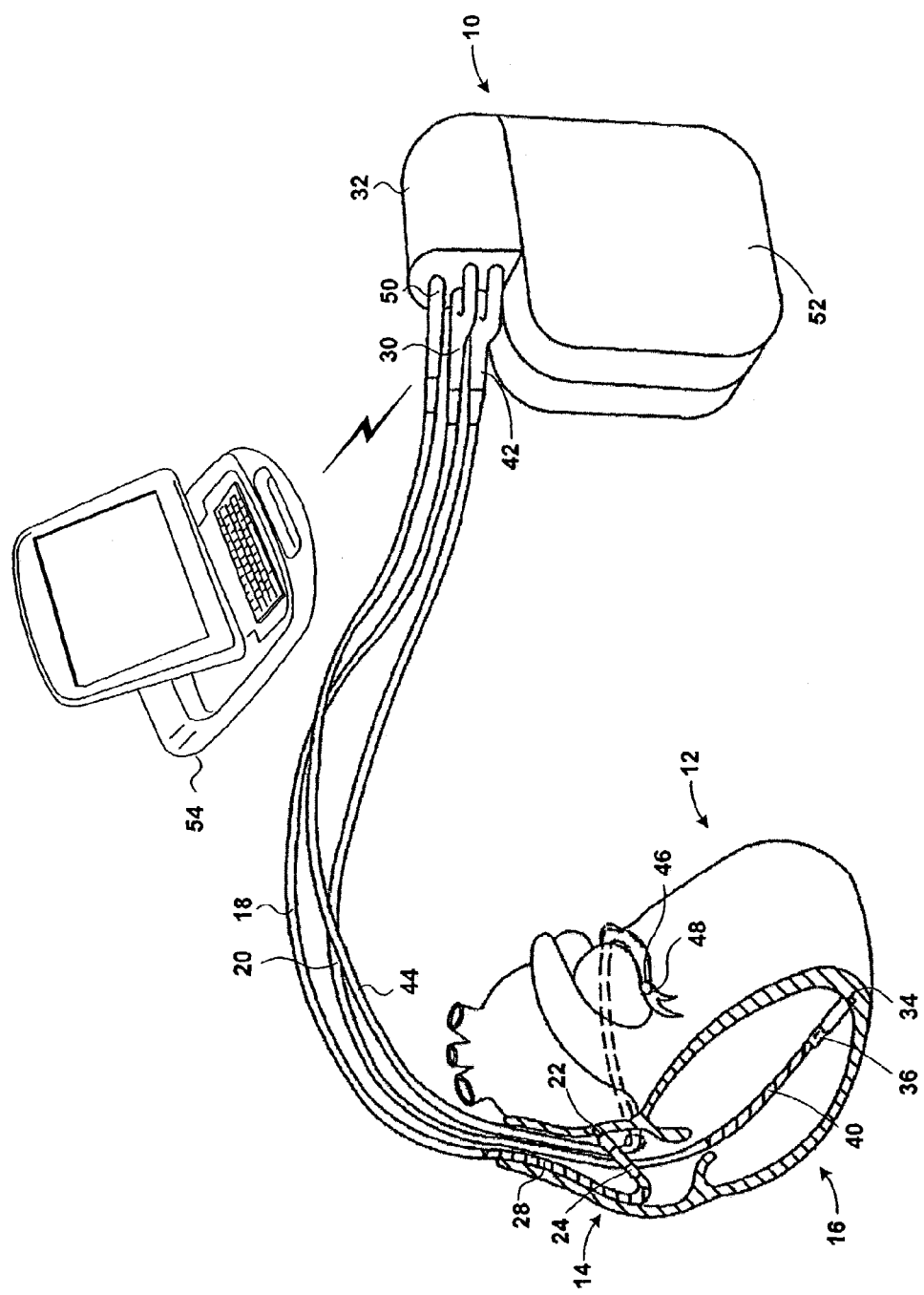
FIG. 1 is a schematic illustration of an atrial and ventricular chamber pacemaker/cardioverter/defibrillator with leads extending to a human heart, and an external programmer.

FIG. 1 depicts an exemplary implantable medical device (IMD) 10 that may practice the techniques of the invention. In the example of FIG. 1, IMD 10 is an implantable multi-chamber pacemaker/cardioverter/defibrillator that includes anti-tachycardia pacing (ATP), cardioversion and defibrillation capability. The invention is not limited to the particular IMD shown in FIG. 1, however, but may be practiced by any number of implantable devices. The techniques of the invention may be practiced by a device that paces and/or shocks a single cardiac chamber or several chambers, that paces and/or shocks one or more atria or one or more ventricles, and that paces in any of several pacing modes. The techniques of the invention may be practiced by any device that is configured to supply ATP therapy and shock therapy.

IMD 10 includes an implantable pulse generator (IPG) (not shown in FIG. 1) that generates pacing stimuli to administer one or more ATP therapies to heart 12. In some circumstances, the IPG may generate pacing stimuli for purposes other than ATP, e.g., to perform antibradycardia pacing. In the embodiment shown in FIG. 1, pacing stimuli may be applied to the right atrium 14 or the right ventricle 16, or both. IMD 10 also includes circuitry to sense atrial and ventricular activations, including activations that may be generated during episodes of atrial tachycardia (AT) or ventricular tachycardia (VT). Atrial and ventricular bipolar pace/sense electrode pairs at the distal ends of leads 18 and 20, respectively, carry out the pacing and sensing functions.

In right atrium 14, the distal end of atrial lead 18 includes a pace/sense tip electrode 22 and a pace/sense ring electrode 24. Pace/sense electrodes 22 and 24 are employed for atrial pacing, including delivery of atrial ATP therapies, and for sensing of P-waves indicative of atrial activation. The distal end of atrial lead 18 also includes an elongated coil defibrillation electrode 28 that can deliver a defibrillation shock to right atrium 14. Electrode 28 may also be used to deliver cardioversion therapy to right atrium 14.

Atrial lead 18 may include conductors that electrically couple electrodes 22, 24 and 28 to IMD 10. The conductors may be arranged coaxially, coradially, in parallel, or in another configuration, and may be insulated from one another and from the tissue of the patient. The proximal end of atrial lead 18 may include a bifurcated connector 30 that couples the conductors to a connector block 32 on IMD 10.

In right ventricle 16, the distal end of ventricular lead 20 likewise may include a pace/sense tip electrode 34 and a pace/sense ring electrode 36. Pace/sense tip electrode 34 is deployed in the apex of heart 12. Pace/sense electrodes 34 and 36 are employed for ventricular pacing, including delivery of ventricular ATP therapies, and for sensing of R-waves indicative of ventricular activation. The distal end of ventricular lead 20 also includes an elongated coil defibrillation electrode 40 that can deliver a defibrillation shock or cardioversion therapy to right ventricle 16.

Defibrillation therapy is painful to the patient. ATP therapies, by contrast, involve far less energy than defibrillation therapy. ATP therapies are often well tolerated by patients, and in some cases, ATP therapies may proceed without the patient becoming aware of the therapies. In some patients, ATP may prevent a tachycardia episode from accelerating into a VF episode, and in this way, ATP may be used to avoid delivery of a painful defibrillation shock.

Like atrial lead 18, ventricular lead 20 may include one or more insulated conductors that electrically couple electrodes 34, 36 and 40 to IMD 10. The proximal end of ventricular lead 20 may include a bifurcated connector 42 that couples the conductors to connector block 32.

FIG. 1 illustrates deployment of a coronary sinus lead 44. Coronary sinus lead 44 may include one or more insulated conductors. The proximal end of coronary sinus lead 44 may include one or more electrodes, such as pace/sense electrode 46. Pace/sense electrode 46 may be deployed within the great vein 48 of heart 12, and may be used to deliver pacing therapies, including ATP therapies, to the left side of heart 12. A connector 50 at the proximal end of the coronary sinus lead 44 couples the conductors in lead 44 to connector block 32. In some embodiments of the invention, coronary sinus lead 44 may include an elongated exposed coil wire defibrillation electrode (not shown).

IMD 10 includes a housing 52 that, in some embodiments of the invention, serves as a "can" electrode. In unipolar operation, IMD 10 may deliver an electrical stimulation to heart 12 via an electrode disposed on one or more of leads 18, 20 or 44, with housing 52 being a part of the return current path. In bipolar operation, by contrast, IMD 10 may deliver an electrical stimulation to heart 12 via a tip electrode, with a ring electrode providing the principal return current path.

In the embodiment depicted in FIG. 1, IMD 10 delivers pacing stimuli to right atrium 14 and right ventricle 16 via electrodes 22 and 34, respectively, and senses activations via the same electrodes. The electrodes sense the electrical activity that accompanies AT, VT and VF. The electrodes also deliver one or more ATP therapies to treat AT or VT.

A clinician interacts with IMD 10 via an external programming device such as a programmer 54. IMD 10 communicates wirelessly with programmer 54, and may download programming instructions pertaining to tachycardia and fibrillation therapies from programmer 54. In particular, a clinician uses programmer 54 to activate various functions pertaining to fibrillation and tachycardia detection and treatment. The invention provides a rapid and efficient arrangement for activating such functions.

A clinician may use programmer 54 to program IMD 10 to administer several ATP therapies. ATP therapies may differ from one another by the manner in which pacing pulses are applied to heart 12 to terminate AT or VT. One ATP therapy, for example, may deliver a sequence of pacing pulses separated from one another by constant time intervals, while another ATP therapy may deliver a sequence of pacing pulses separated from one another by time intervals that shorten with each pulse in the series. The number of pulses in the ATP therapies may vary from one therapy to another.

The invention provides techniques for automatic activation of VT therapies, which may include delivery of ATP and/or shocks, when a clinician executes a single command, such as a command to activate VF therapies or a command to activate VF detection. Instead of activating each VF and VT therapy individually, a clinician may activate the therapies in a set. In addition, the clinician may activate one or more hierarchies of ATP therapies in a set. Techniques for activating multiple therapies will be described in more detail below.

Figure 2:
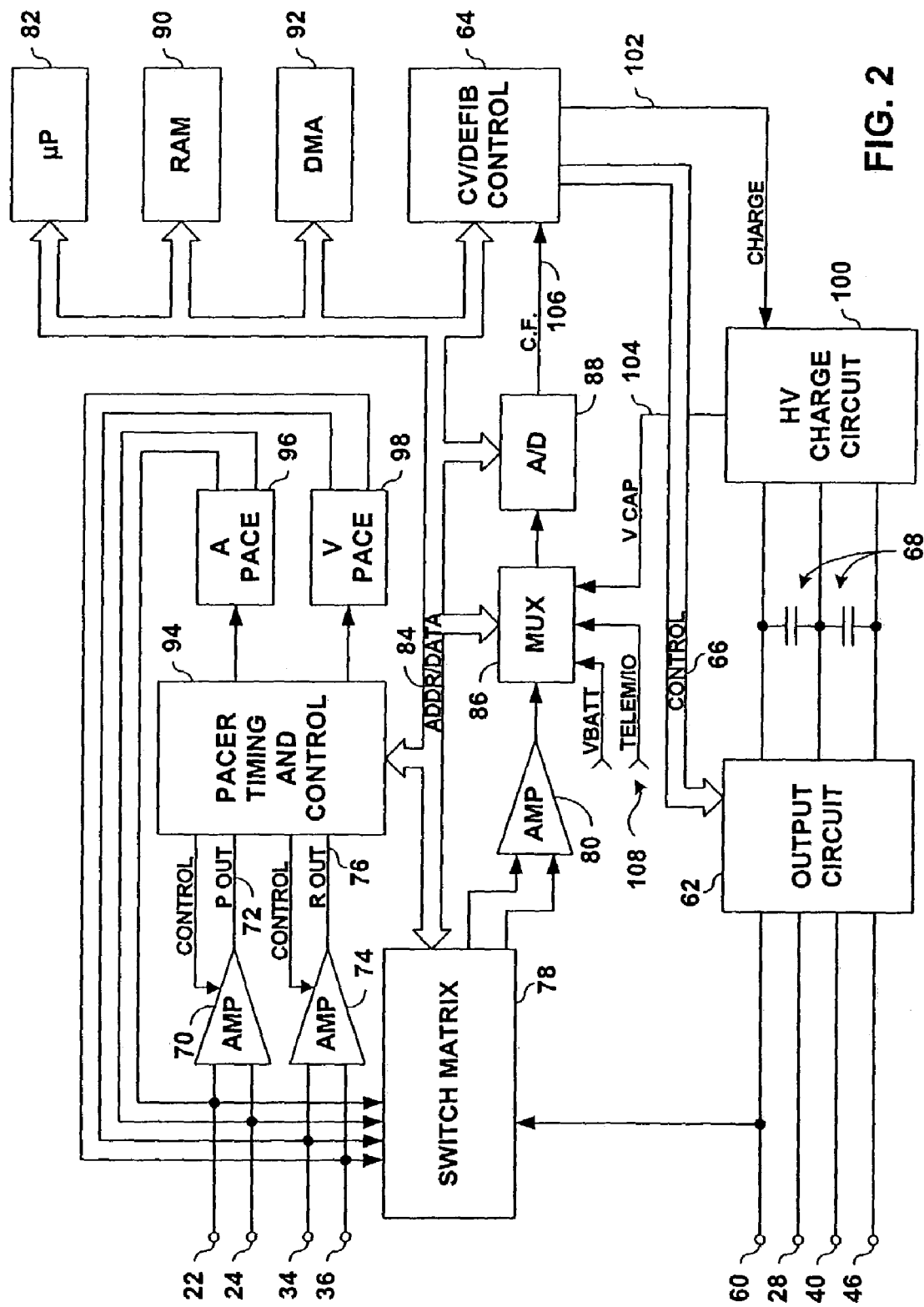
FIG. 2 is a block diagram of the implantable medical device depicted in FIG. 1.

FIG. 2 is a functional schematic diagram of one embodiment of IMD 10 and illustrates how IMD 10 detects episodes of VF and tachycardia, and delivers therapies, such as shocks and ATP, to address the episodes. This diagram is exemplary of the type of device in which various embodiments of the invention may be embodied, and the invention is not limited to the particular schematic shown. On the contrary, the invention may be practiced in a wide variety of devices, including single- and multi-chamber devices.

FIG. 2 includes electrode terminals 22, 24, 28, 34, 36, 40 and 46, which correspond to the electrodes shown in FIG. 1. Electrode 60 corresponds to the uninsulated portion of housing 52 of IMD 10. Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation or cardioversion shocks.

Electrodes 22 and 24, located on or in right atrium 14, are coupled to a P-wave amplifier 70. Amplifier 70 may comprise an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold. The time intervals between signals on P-out line 72 reflect the cycle length of atrial activations, and may be indicative of whether the patient is experiencing an episode of AT. In particular, short cycle lengths may be indicative of AT.

Electrodes 34 and 36, located in right ventricle 16, are coupled to an R-wave amplifier 74. Amplifier 74 may comprise an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74. The time intervals between signals on R-out line 76 reflect the cycle length of ventricular activations and may be indicative of whether the patient is experiencing an episode of VT or VF.

A switch matrix 78 may select electrodes for coupling to a wide band amplifier 80 for use in digital signal analysis. Selection of electrodes is controlled by microprocessor 82 via data/address bus 84. The signals from the selected electrodes are provided to multiplexer 86, and are thereafter converted to multi-bit digital signals by A/D converter 88. The signals may be stored in random access memory (RAM) 90 under control of direct memory access (DMA) circuit 92.

Digital signal analysis includes, but is not limited to, a morphological analysis of waveforms sensed by the selected electrodes. Morphological analysis may comprise wavelet analysis, Fourier analysis or similar spectral analysis techniques, but the invention is not limited to those analytical techniques. Microprocessor 82 may employ digital signal analysis techniques to characterize the digitized signals stored in RAM 90 to recognize and classify the patient's heart rhythm or to determine the morphology of the signals employing any of several signal-processing methodologies.

Signals sensed via electrodes 22, 24, 34 and 36 may be used to determine whether to administer cardiac pacing, ATP, cardioversion or defibrillation therapies. Pacer timing/control circuitry 94 receives signals from P-out line 72 and R-out line 76, and computes various timing intervals as a function of the timing of the received signals. Pacer timing/control circuitry 94 also may include programmable digital counters that control pacing according to any of several pacing modes.

Pacer output circuitry 96 and 98, which are coupled to electrodes 22, 24, 34 and 36, generate pacing and ATP stimuli under the control of pacer timing/control circuitry 94. The IPG of IMD 10 comprises microprocessor 82, in cooperation with pacer timing/control circuitry 94 and pacer output circuitry 96 and 98.

Pacer timing/control circuitry 94 may also compute intervals such as R-R intervals, P-P intervals, P-R intervals and R-P intervals. These intervals may be used to detect the presence of a fast heart rate, which may be an indicator of a tachycardia. A fast heart rate may also be indicative of sinus tachycardia, i.e., a fast heart rate in response to a physiological stimulus, such as exercise. Microprocessor 82 and pacer timing/control circuitry 94 may cooperate to apply any of a number of algorithms to discriminate a tachycardia such as VT or AT, for which antitachycardia therapy may be indicated, from sinus tachycardia, for which therapy is not indicated. Microprocessor 82 and pacer timing/control circuitry 94 may further cooperate to apply any of a number of algorithms to discriminate a tachycardia such as AT or VT, which may terminate in response to antitachycardia therapies, from atrial fibrillation (AF) and VF, which generally do not respond to ATP therapies. The invention may be practiced with any algorithm or algorithms that detect an atrial or ventricular tachycardia.

When IMD 10 detects an atrial or ventricular tachycardia, microprocessor 82 may select an ATP regimen that comprises a plurality of ATP therapies arranged in a hierarchy. In general, the first ATP therapy in a hierarchy is applied initially. If the first ATP therapy fails to terminate the tachycardia, the second ATP therapy in the hierarchy is applied, and so on. RAM 90 may store one or more hierarchies.

For each ATP therapy that is applied, microprocessor 82 loads parameters such as timing intervals from RAM 90 into pacer timing/control circuitry 94, which controls delivery of the ATP therapy. Microprocessor 82 evaluates the outcome of the ATP therapy, and determines whether ATP therapy should be discontinued or whether the next therapy in the hierarchy ought to be applied.

In some circumstances, a tachycardia may be unresponsive to all ATP therapies in the selected hierarchy. In some of those circumstances, cardioversion may be indicated. When microprocessor 82 or pacer timing/control circuitry 94 detect VF, defibrillation shocks are indicated.

When a cardioversion or defibrillation shock is required, microprocessor 82 may control the timing, strength and duration of the shocks. In response to the detection of atrial or ventricular fibrillation or tachycardia requiring a cardioversion pulse, microprocessor 82 activates CV/defib control circuitry 64, which initiates charging of capacitor bank 68 via charging circuit 100, under the control of high voltage charging control line 102. The voltage on the high voltage capacitors is monitored via VCAP line 104, which is passed through multiplexer 86, and in response to reaching a predetermined value set by microprocessor 82, results in generation of a logic signal on Cap Full (CF) line 106 to terminate charging. A defibrillation or cardioversion pulse may be delivered by output circuit 62.

IMD 10 includes a telemetry unit 108 that supports wireless communication with an external device such as programmer 54 (not shown in FIG. 2). IMD 10 may upload data via telemetry unit 108 and may also download data and programming via telemetry unit 108. In particular, IMD 10 receives programming pertaining to tachycardia and fibrillation therapies via telemetry unit 108. Telemetry unit 108 may communicate wirelessly with an external device via radio frequency communication, magnetic communication, ultrasound communication or any other communication technique.

Figure 3:
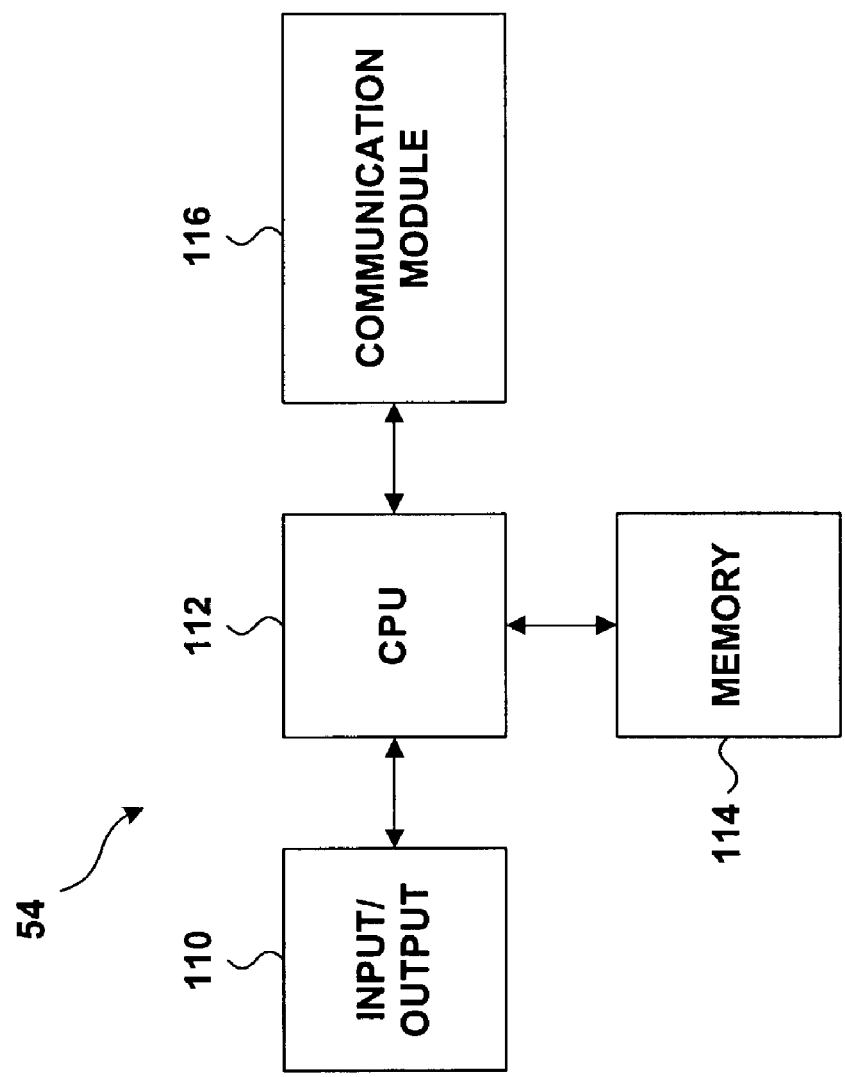
FIG. 3 is a block diagram of the programmer depicted in FIG. 1.

FIG. 3 is a functional schematic diagram of one embodiment of programmer 54 and illustrates how programmer 54 programs IMD 10. A clinician interacts with programmer 54 via one or more input/output devices 110, such as a keyboard, display screen, touch screen, or pointing tool such as a mouse. A central processing unit (CPU) receives input from and supplies output to input/output device 110. CPU 112 also supervises the operation of programmer 54, particularly setting a group of VF- and VT-related functions to active status, as will be described below. The functions may be retrieved from and stored in memory 114, which may comprise RAM or a storage medium. Memory 114 stores default functions and modifications to default functions, as described in more detail below. Memory 114 may further store instructions that will program IMD 10.

A communications module 116 is configured to establish a communication link between programmer 54 and IMD 10. As noted above, communication may be wireless and may take advantage of radio frequency communication, magnetic communication, ultrasound communication or any other communication technique. Programmer 54 may download programming instructions pertaining to tachycardia and fibrillation therapies to IMD 10 via communications module 116. In particular, programmer 54 may download instructions that set a group of functions to active status.

Figure 4:
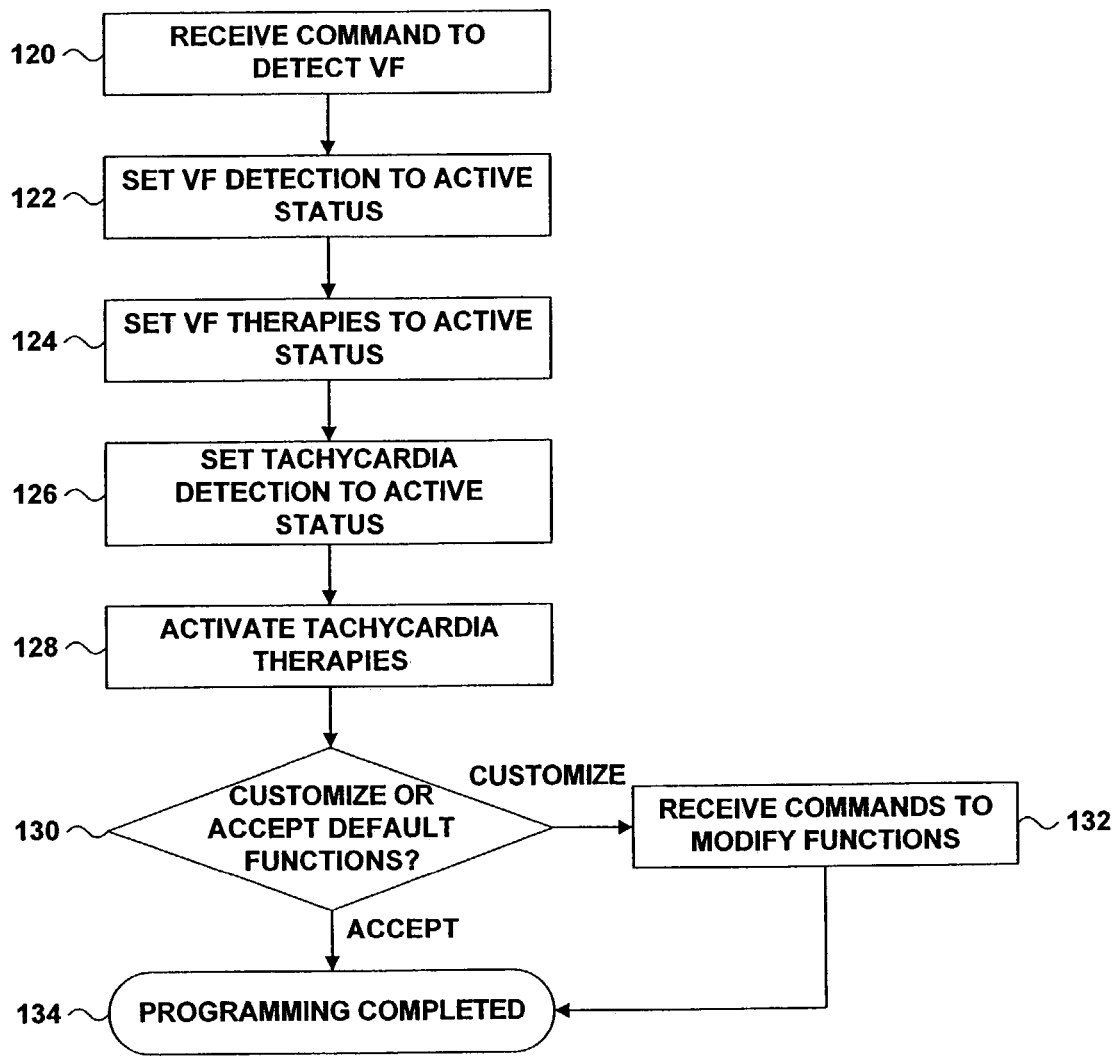
FIG. 4 is a flow diagram illustrating exemplary techniques for activating multiple fibrillation and tachycardia functions of an IMD with a programmer.

FIG. 4 is a flow diagram illustrating an exemplary technique for carrying out the invention. The technique has application in the context of a clinician entering instructions into programmer 54, which in turn programs IMD 10. In a typical application, the clinician programs instructions into programmer 54, which stores the instructions in memory as a batch. Programmer 54 then establishes communication with IMD 10 and programs IMD 10 with the batch of instructions. The invention also encompasses applications in which programmer 54 receives an instruction from the clinician and relays each instruction interactively to IMD 10.

When programmer 54 receives a command to activate VF detection (120), programmer 54 sets VF detection algorithms in IMD 10 to active status (122). Programmer 54 need not activate VF detection algorithms in IMD 10 immediately upon receipt of the command to set the VF detection algorithms to active status. Instead, programmer 54 may include one or more programming instructions to activate VF detection algorithms in a batch of instructions that will be downloaded to IMD 10 in the future. The invention also encompasses applications in which setting the VF detection algorithms to active status include activating the VF detection algorithms in IMD 10 right away.

In addition, programmer 54 sets other functionality of IMD 10 to active status as well. Programmer 54 sets the VF therapies to active status automatically (124), without a separate activation command for each VF therapy. Programmer 54 further automatically sets tachycardia detection (126) and tachycardia therapies (128) to active status without separate activation commands.

In other words, turning VF detection "on" also automatically activates a group of "default" VF therapies, tachycardia detection and VT therapies. The VF therapies may include a hierarchy of two or more VF therapies. The VT therapies may include a hierarchy of two or more ATP therapies, and may also include shocks. A single command by a clinician to set one function to active status thereby turns several related functions "on."

In a variation of this technique, programmer 54 may receive a single command to set a group of VF- and VT-related functions to active status. In other words, the clinician may give a single command that operates as a "master 'on'" command. The "master 'on'" command need not make reference to any particular VF- and VT-related function.

Once the VF- and VT-related functions are set to active status, the clinician may elect to customize the functions to the particular patient. After IMD 10 receives the clinician's command to customize the functions (130), IMD 10 receives commands from the clinician to modify the default functions (132). The clinician may, for example, set particular therapies to active status and deactivate others, or change the order of therapies in the hierarchies. When the customization is completed, or when IMD 10 receives the election of the clinician to accept the chosen functions, then programmer 54 completes the programming (134). Completing the programming (134) may include establishing a wireless communication link with IMD 10 and downloading the batch of instructions to IMD 10, thereby programming IMD 10.

The manufacturer of IMD 10 or programmer 54 may supply default VF detection routines, VF therapies, VT detection and VT therapies, and the default hierarchies of therapies. A particular clinician, however, may wish to tailor the default functions to meet the needs of the clinician's patients. As shown in FIG. 4, the clinician may customize the functions to a particular patient, but some clinicians may find themselves performing exactly the same customization for most or all patients. In other words, the clinician may wish to customize the default functions for a set of patients so that the clinician may avoid the patient-by-patient customization shown in FIG. 4.

Figure 5:
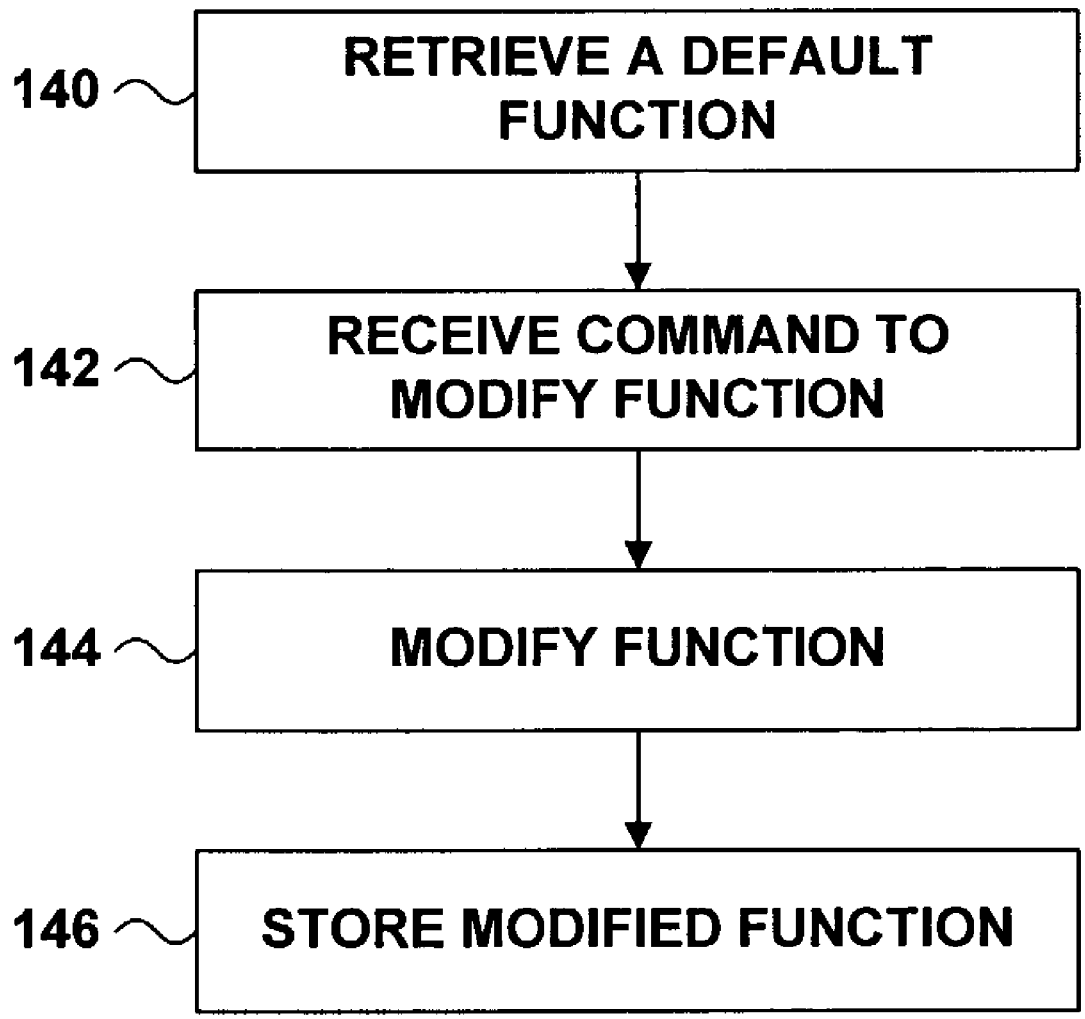
FIG. 5 is a flow diagram illustrating exemplary techniques for modifying default fibrillation and tachycardia functions.

FIG. 5 is a flow diagram illustrating a technique for customizing the therapies or other functions to suit the practice of a clinician. In general, programmer 54 may, at the direction of the clinician, retrieve a default function (140), i.e., one or more programming instructions pertaining to ventricular fibrillation therapy or VT therapy. Programmer 54 further receives one or more commands to modify the function (142) and modifies the function according to the commands (144). Programmer stores the modified function in memory (146) as an updated default function.

This technique may be illustrated in the context of a hierarchy of ATP therapies. A programmer holds a default hierarchy of ATP therapies, such as a hierarchy supplied by the manufacturer of IMD 10 or programmer 54. The clinician prefers to apply ATP therapies in a hierarchy that is different from the currently existing default hierarchy.

Programmer 54 retrieves the hierarchy from memory (140), and receives one or more commands to modify the hierarchy (142). Programmer 54 modifies the hierarchy according to the commands (144) and stores the modified hierarchy in memory (146). When the clinician subsequently activates VF- and VT-related functions for a particular IMD, programmer 54 applies the modified default hierarchy, rather than the original default hierarchy supplied by the manufacturer.

The techniques shown in FIG. 5 may be applied to customization of other VF- and VT-related functions as well. The clinician may choose to customize individual therapies by, for example, setting the number of initial pulses in a therapy. The clinician may also choose to set particular therapies to active status, and leave others deactivated.

Figure 6:
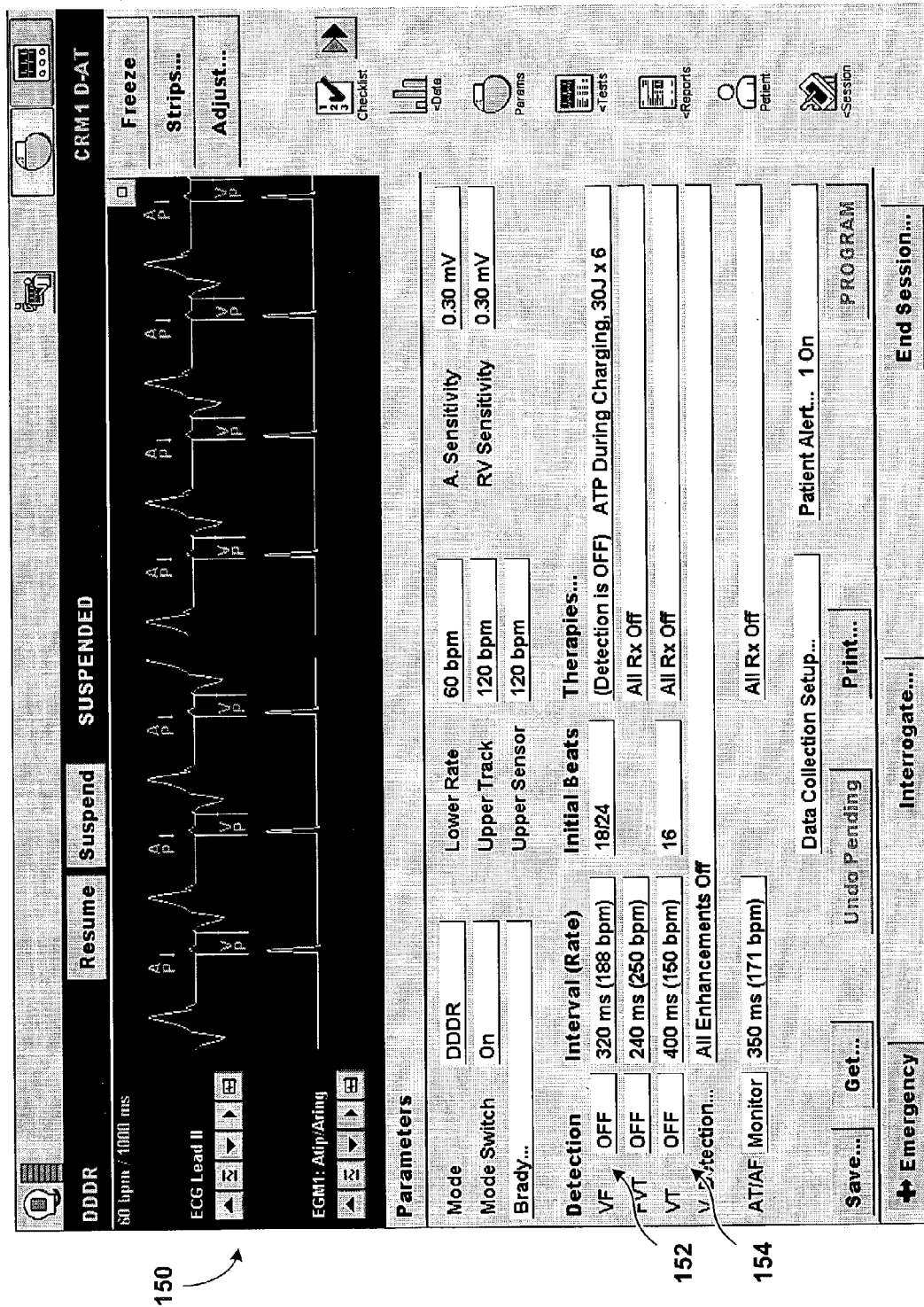
FIG. 6 is an exemplary screen display from a programmer, illustrating fibrillation and tachycardia functions as "off."

FIG. 6 is an exemplary screen display 150 on a device such as programmer 54. Display 150 shows several options for activating therapies, including VF therapies and VT therapies. As shown in FIG. 6, VF detection 152 is "off," as is VT detection 154.

Figure 7:
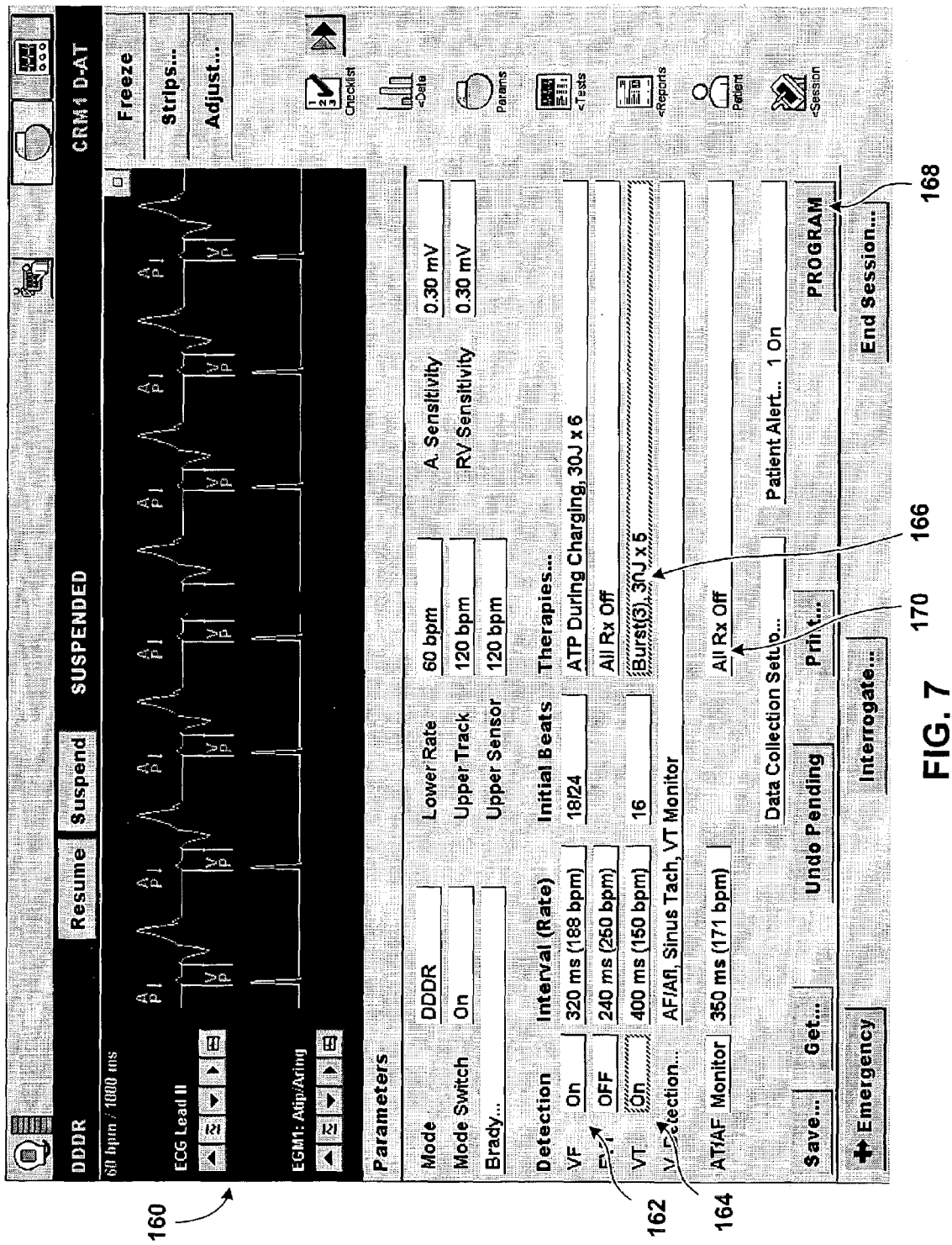
FIG. 7 is an exemplary screen display from a programmer, illustrating fibrillation and tachycardia functions as "on" following activation of a single function.

FIG. 7 is an exemplary screen display 160 that illustrates how the options may change after activation of a single function. In FIG. 7, VF detection 162 has been set to active status, i.e., turned "on." As a result, VT detection 164 has also been turned "on" without a separate command. In addition, at least one VT therapy 166 has been automatically selected, without a separate command. By selecting the "Program" option 168, a clinician may download these instructions as a batch to an IMD.

As a result of changing a single field on screen display 150, several fields on screen display 160 have been automatically filled with default instructions. A clinician no longer needs to take the time to fill in each field individually, although the clinician may nevertheless choose to do so. The default instructions need not activate all possible therapies. For instance, as shown in FIG. 7, activation of VF detection 162 has not resulted in the activation of atrial therapies 170.

Screen displays 150 and 160 are for purposes of illustration, and the invention is not limited to the particular information shown. The screen display may include, for example, a detailed hierarchy of therapies that become automatically activated upon a single command. The parameters of each individual therapy may be displayed, such as the order of the therapy in the hierarchy, whether the therapy is on or off, whether the therapy is a burst or a ramp, the number of initial stimulating pulses in the therapy, and so forth. Upon receiving a single command to set a group of functions to active status, programmer 54 may set each of the parameters automatically. The clinician need not individually program the parameters on a patient-by-patient basis.

Screen display 150 may also include a "master 'on'" option. For example, the screen display may include a single button saying "Activate ventricular therapies" that, when selected, automatically activates VF- and VT-related functions.

The techniques of the invention may save time for the clinician by activating several functions with a reduced number of commands. As a result, a clinician may program an IMD more quickly and more efficiently. A clinician may tailor the functions to the particular needs of the patient, as well as to the particular preferences of the clinician.

In some circumstances, the invention provides added patient safety. Some programmers and IMDs allow a clinician to activate detection of VF, and require a separate activation of therapies for VF. The invention may be implemented so that activation of VF detection automatically activates VF therapies. In this way, there is less risk to the patient that a clinician may activate detection but inadvertently fail to activate therapy.

The invention further provides patient benefits. Many patients at risk of VF are also at risk of VT. When programming an IMD in a conventional manner, the clinician may be deterred from programming an ATP hierarchy of therapies for the patient because of the time and complexity of the programming. With the invention, however, a default hierarchy of VT therapies may be activated without the time and complexity of individual programming. As a result, the IMD in the patient is more likely to have VT therapies activated, in addition to VF therapies. Not only does the patient receive the benefit or additional functionality of the IMD, activation of VT therapies may cause the patient to experience fewer episodes of VF, because some ATP therapies for VT are known to terminate episodes of VT that may accelerate into VF. Furthermore, ventricular ATP therapies are considerably less painful to the patient than defibrillation shocks, so application of the invention may cause the patient to experience fewer episodes of VF and fewer painful shocks.

The preceding specific embodiments are illustrative of the practice of the invention. Various modifications may be made without departing from the scope of the claims. For example, some of the techniques described above may be embodied as a computer-readable medium comprising instructions for a programmable processor such as microprocessor 82 or pacer timing/control circuitry 94 shown in FIG. 2, or CPU 112 shown in FIG. 3. The programmable processor may include one or more individual processors, which may act independently or in concert. A "computer-readable medium" includes but is not limited to read-only memory, Flash memory and a magnetic or optical storage medium. These and other embodiments are within the scope of the following claims.

The invention claimed is:

1. A computer readable medium having computer executable instructions for performing a method for programming a medical device (IMD) capable of selectively delivering a ventricular fibrillation (VF) therapy and a ventricular tachycardia (VT) therapy, the method comprising:
   sending a command to the IMD to initially program a VF therapy delivery function to an active status from an inactive status; and
   automatically activating a VT therapy delivery function to an active status from an inactive status due to the VF therapy delivery function being initially programmed to an active status from an inactive status,
   wherein the VF therapy delivery function is different from the VT therapy delivery function.

2. The computer readable medium of claim 1, wherein the ventricular tachycardia therapy comprises at least one of an antitachycardia pacing therapy, a hierarchy of antitachycardia pacing therapies, and a cardioversion shock.

3. The computer readable medium of claim 1, wherein the command sent to the IMD to initially activate the VF therapy delivery function to an active status automatically activates a group of default VF therapies without a separate activation command for each VF therapy.

4. The computer readable medium of claim 3, wherein the group of default VF therapies includes a hierarchy of at least two VF therapies.

5. The computer readable medium of claim 1, wherein activating the VT therapy delivery function when the VF therapy delivery function is initially programmed to an active status from the inactive status automatically activates a group of default VT therapies without a separate activation command for each VT therapy.

6. The computer readable medium of claim 5, wherein the group of default VT therapies includes a hierarchy of antitachycardia pacing therapies.

7. The computer readable medium of claim 1, wherein the command to the IMD to initially program the VF therapy delivery function to an active status from the inactive status operates as a master "on" command.

8. The computer readable medium of claim 7, wherein the command sent to the IMD to initially activate the VF therapy delivery function to an active status automatically activates a group of default VF therapies without a separate activation command for each VF therapy and wherein activating the VT therapy delivery function when the VF therapy delivery function is initially programmed to an active status from the inactive status automatically activates a group of default VT therapies without a separate activation command for each VT therapy.

9. The computer readable medium of claim 8, further comprising the step of sending a command to the IMD to modify the default VF therapies and the default VT therapies to customize the VF therapy and VT therapy delivery functions.

10. The computer readable medium of claim 9, wherein sending the command to the IMD to modify the default VF therapies and the default VT therapies comprises the steps of setting particular therapies to active status, setting particular therapies to inactive status, and changing the order of therapies in a hierarchy of therapies.

11. The computer readable medium of claim 1, wherein the command to the IMD to initially program the VF therapy delivery function to an active status from the inactive status comprises a batch of instructions downloaded to the IMD.

* * * * *